(12) United States Patent
Lee et al.

(10) Patent No.: US 10,792,509 B2
(45) Date of Patent: Oct. 6, 2020

(54) DISPLAY APPARATUS AND DISPLAY SYSTEM

(71) Applicant: SAMSUNG DISPLAY CO., LTD., Yongin-si, Gyeonggi-Do (KR)

(72) Inventors: Changhoon Lee, Yongin-si (KR); Jongsung Bae, Yongin-si (KR); Jongin Baek, Yongin-si (KR); Yijoon Ahn, Yongin-si (KR)

(73) Assignee: SAMSUNG DISPLAY CO., LTD., Yongin-si, Gyeonggi-Do (KR)

( * ) Notice: Subject to any disclaimer, the term of this patent is extended or adjusted under 35 U.S.C. 154(b) by 1213 days.

(21) Appl. No.: 15/089,762

(22) Filed: Apr. 4, 2016

(65) Prior Publication Data
US 2017/0080250 A1    Mar. 23, 2017

(30) Foreign Application Priority Data
Sep. 22, 2015  (KR) .......................... 10-2015-0133884

(51) Int. Cl.
*A61N 5/06*  (2006.01)

(52) U.S. Cl.
CPC ......... *A61N 5/0616* (2013.01); *A61N 5/0618* (2013.01); *A61N 2005/0626* (2013.01); *A61N 2005/0659* (2013.01); *A61N 2005/0661* (2013.01); *A61N 2005/0663* (2013.01)

(58) Field of Classification Search
CPC ................ A61N 5/0616; A61N 5/0618; A61N 2005/0626; A61N 2005/0659; A61N 2005/0661; A61N 2005/0663

USPC ............................................................ 607/88
See application file for complete search history.

(56) References Cited

U.S. PATENT DOCUMENTS

| | | | |
|---|---|---|---|
| 2009/0143842 A1 | 6/2009 | Cumbie et al. | |
| 2010/0283969 A1 | 11/2010 | Cooperstock et al. | |
| 2011/0164122 A1 | 7/2011 | Hardacker | |
| 2013/0066404 A1 | 3/2013 | Tapper et al. | |
| 2015/0039061 A1 | 2/2015 | Hong et al. | |
| 2015/0051672 A1 | 2/2015 | Jo et al. | |
| 2015/0324981 A1* | 11/2015 | Kim .................... | A61N 5/0618 345/619 |
| 2016/0021366 A1 | 1/2016 | Lee et al. | |

FOREIGN PATENT DOCUMENTS

| | | |
|---|---|---|
| KR | 1020140075706 | 6/2014 |
| KR | 1020150014659 | 2/2015 |
| KR | 1020150020870 | 2/2015 |
| KR | 1020160009166 | 1/2016 |

* cited by examiner

*Primary Examiner* — Aaron F Roane
(74) *Attorney, Agent, or Firm* — F. Chau & Associates, LLC

(57) ABSTRACT

A display apparatus includes a display; an image processor which generates a first image including sequential first frame data and a second image including sequential second frame data; an image data generator which generates image data comprising the first frame data and the second frame data alternately; and a control signal generator which generates a shutter glasses control signal that opens shutters for both eyes of a first pair of shutter glasses when the first frame data is displayed on the display, and that closes the shutters for both eyes of the first pair of shutter glasses when the image data including the second frame data is displayed on the display.

20 Claims, 11 Drawing Sheets

DISPLAY APPARATUS AND DISPLAY SYSTEM

CROSS-REFERENCE TO RELATED APPLICATION

This application claims priority under 35 U.S.C. § 119 to Korean Patent Application No. 10-2015-0133884, filed on Sep. 22, 2015, in the Korean Intellectual Property Office KIPO, the disclosure of which is incorporated by reference in its entirety herein.

BACKGROUND

1. Technical Field

One or more exemplary embodiments of the inventive concept relate to a display apparatus and a display system.

2. Discussion of Related Art

Light therapy consists of exposure to daylight or to specific wavelengths of light. The light from the therapy may be applied to the skin of a human body or to the retina of an eye of a human being. When such light is applied to the skin of a human body, it may have a positive effect on the skin. However, when such light is exposed to the eye of a human being, it may have an adverse effect on the eye.

Someone with a color vision deficiency has a decreased ability to see color or perceive color differences, under normal lighting conditions. Therefore, an individual with a color vision deficiency (e.g., a color-weak person) may have trouble seeing the displayed image.

SUMMARY

At least one embodiment of the present invention provides a display apparatus which is configured to enable a viewer, while viewing an information image, to receive light therapy without adversely affecting the eyes.

An exemplary embodiment of the present invention provides a display apparatus which may enable a color-weak person and someone who is not a color-weak person to view the image at the same time and get light therapy without affecting the eyes.

According to an exemplary embodiment of the present invention, a display apparatus includes a display; an image processor which generates a first image including sequential first frame data and a second image including sequential second frame data; an image data generator which generates image data including the first frame data and the second frame data alternately; and a control signal generator which generates a shutter glasses control signal that opens shutters for both eyes of a first pair of shutter glasses when the first frame data is displayed on the display, and that closes shutters for both eyes of the first pair of shutter glasses when the second frame data is displayed on the display.

According to an exemplary embodiment of the present invention, a display system includes a display apparatus including a display, an image processor which generates a first image including sequential first frame data and a second image including sequential second frame data; an image data generator which generates image data including the first frame data and the second frame data alternately, and a control signal generator which generates a shutter glasses control signal that opens shutters for both eyes of a first pair of shutter glasses when the first frame data is displayed on the display, and that closes shutters for both eyes of the first pair of shutter glasses when the second frame data is displayed on the display; and a first pair of shutter glasses that opens or closes shutters for both eyes simultaneously by receiving the shutter glasses control signal.

According to an exemplary embodiment of the present invention, a display apparatus is provided including a display which displays a first image and a second image alternately by each frame data; and a control signal generator which generates a shutter glasses control signal that opens the shutters for both eyes of the first pair of shutter glasses when the first image is displayed on the display, and that closes the shutters for both eyes of the first pair of shutter glasses when the second image is displayed on the display.

According to an exemplary embodiment of the present invention, a display apparatus is provided that includes a display and a control signal generator. The display is configured to display a first image, a second image, and a third image alternately. The control signal generator is configured to generate a shutter glasses control signal that opens first shutters for both eyes of a first pair of glasses and closes second shutters for both eyes of a second pair of shutter glasses when the first image is displayed on the display, that closes the first and second shutters when the second image is displayed on the display, and that closes the first shutters and opens the second shutters when the third image is displayed on the displayed.

A display apparatus and a display system, according to an exemplary embodiment of the present invention, may enable the viewer, while viewing the information image, to receive light therapy without adversely affecting their eyes.

In some embodiments, a color-weak person and someone who is not a color-weak person may view the image at the same time and receive light therapy without adversely affecting their eyes.

BRIEF DESCRIPTION OF THE DRAWINGS

The inventive concept will become apparent and more readily appreciated from the following description of the exemplary embodiments thereof, taken in conjunction with the accompanying drawings in which.

DETAILED DESCRIPTION

Figure 1:
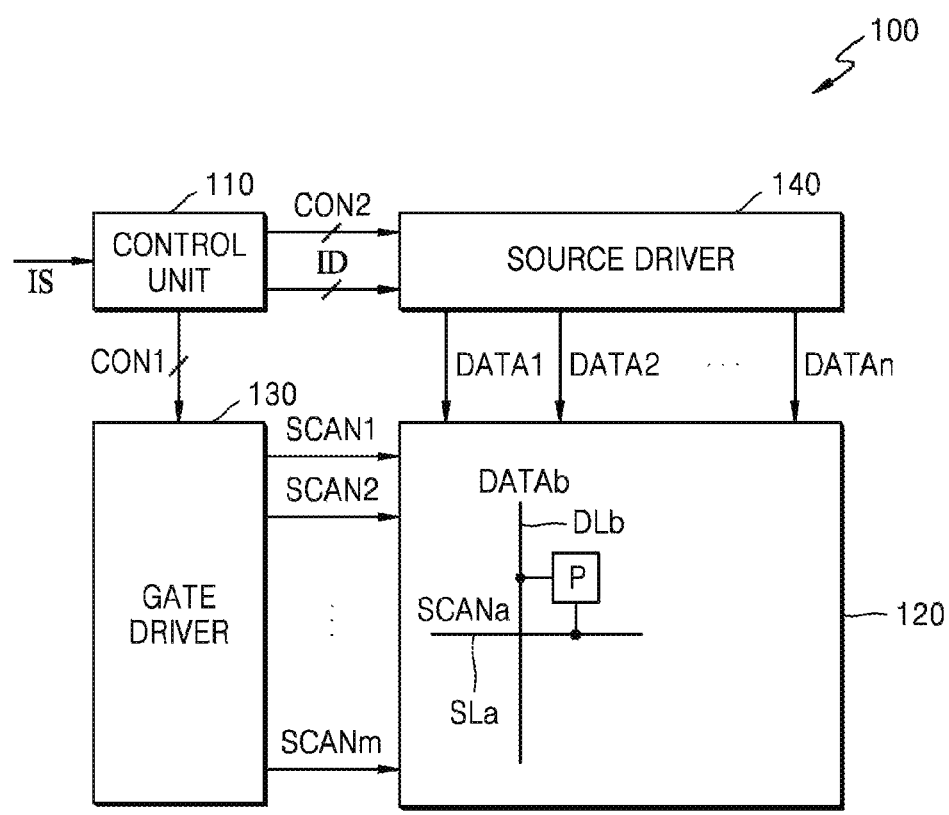
FIG. 1 is a block diagram of a display apparatus, according to an exemplary embodiment of the inventive concept.

As the invention allows for various changes and numerous embodiments, exemplary embodiments will be illustrated in the drawings and described in detail in the written description. This invention may, however, be embodied in many different forms and should not be construed as limited to the exemplary embodiments set forth herein.

Hereinafter, the present invention will be described in detail by explaining exemplary embodiments of the invention with reference to the attached drawings. In explaining exemplary embodiments of the invention by referring to the drawings, the same reference numerals will be given to the same or corresponding components, and redundant explanation will be omitted.

As used herein, the singular forms "a," "an" and "the" are intended to include the plural forms as well, unless the context clearly indicates otherwise.

FIG. 1 is a block diagram of a display apparatus 100 according to an exemplary embodiment of the inventive concept.

Referring to FIG. 1, the display apparatus 100 according to the present embodiment includes a control unit 110 (e.g., a controller or control circuit), a display 120, a gate driver 130 (e.g., a gate or scan line driving circuit), and a source driver 140 (e.g., a source or data line driving circuit). The control unit 110, the gate driver 130, and the source driver 140 may be formed either on separate semiconductor chips respectively or on a same single semiconductor chip. In an exemplary embodiment, the control unit 110, the gate driver 130, and/or the source driver 140 are formed on the same substrate together with the display 120.

The display apparatus 100 may be a liquid crystal display (LCD) apparatus, an organic light-emitting display (OLED) apparatus, a flexible display, a 3-dimentional (3D) display, or an electrophoretic display. However, the scope of the present invention is not limited thereto, and the display apparatus 100 of the present invention may be various electronic devices which provide visual information by emitting light.

The display apparatus 100, for example, may be an electronic device such as a wearable display, a smartphone, a tablet computer, a personal computer (PC), a laptop PC, a monitor, or a TV.

The display apparatus 100 may display a picture image through a pixel P. The pixel P may include a plurality of sub-pixels respectively representing a plurality of colors to display a variety of colors. Hereinafter, the pixel P may mainly mean one sub-pixel. However, embodiments of the present invention are not limited thereto, and the pixel P may mean a pixel unit which includes the plurality of sub-pixels. That is, although it is described that there is one pixel P herein, it may be construed that a pixel unit may include one sub-pixel or several sub-pixels.

In an embodiment where the display apparatus 100 emits light due to self-emission of the pixel P, the pixel P includes a light-emitting device and a pixel circuit. The pixel circuit may receive a driving voltage and a data signal, and supply a driving current to the light-emitting device. In this embodiment, the driving voltage includes a first driving voltage and a second driving voltage. The first driving voltage may be a driving voltage which has a relatively high level while the second driving voltage may be a driving voltage which has a relatively low level. The level of the driving voltage provided to the pixel P may be a value between the level of the first driving voltage and that of the second driving voltage. In an embodiment where the display apparatus 100 includes a separate light-emitting device such as a backlight, the pixel P includes a device which controls light transmittance such as a liquid crystal, a pixel circuit providing driving power to the device which controls light transmittance, and a color filter.

The display apparatus 100 may receive a plurality of external image data, where the image data includes data for multiple image frames. The image data may allow a video image to be displayed when the plurality of image frames are displayed sequentially. The image data for the plurality of image frames may include image content IS (e.g., image data or an image data signal). The image content IS may include information on a luminance of light emitted by the pixel P (e.g., a level of the luminance), and the number of bits of the image content IS may depend on a level of the luminance. For example, in an embodiment where the number of luminance levels of light emitted by the pixel P is 256, the image content IS may be an 8-bit digital signal. In an embodiment where the darkest gradation displayed through the display 120 is at a $1^{st}$ level and the brightest gradation displayed through the display 120 is at a $256^{th}$ level, the image content IS signal corresponding to the $1^{st}$ level is 0 and the image content signal IS corresponding to the $256^{th}$ level is 255. The darkest gradation displayed by the display 120 may be referred to as a minimum gradation value and the brightest gradation may be referred to as a maximum gradation value. The number of luminance levels of light emitted by the pixel P is not limited to 256 and may vary in alternate embodiments. Examples of the number of luminance levels that can be emitted by a pixel include 32, 64, 128, 512, and 1024.

The control unit 110 may be connected to the display 120, the gate driver 130, and the source driver 140. The control unit 110 may be provided with an input of the image content IS and may transmit first control signals CON1 to the gate driver 130. The first control signals CON1 may include a horizontal synchronization signal (HSYNC). The first control signals CON1 may include control signals required for the gate driver 130 to transmit scanned signals SCAN1 through SCANm, which synchronize with the HSYNC. The control unit 110 may transmit second control signals CON2 to the source driver 140.

The control unit 110 may transmit image data ID (e.g., an image signal) to the source driver 140. The second control signals CON2 may include control signals required for the source driver 140 to transmit data signals DATA1 through DATAn corresponding to the image data ID. The image data ID may include image information required to generate data signals DATA1 through DATAn. The image data ID may be image data which is generated by compensating image content IS received from an outside source.

The display 120 may include a plurality of pixels, a plurality of scan lines respectively connected to pixels positioned in a row among the plurality of pixels, and a plurality of data lines respectively connected to pixels positioned in a column among the plurality of pixels. For example, as shown in FIG. 1, the display 120 may include the pixel P which is included among the plurality of pixels. In this embodiment, the pixel P may be disposed at an A-th row and a B-th column of the display 120. In this embodiment, the display 120 may include an A-th scan line (SLa) which is connected to all pixels positioned on the A-th row, and a B-th data line (DLb) which is connected to all pixels positioned on the B-th column. In this embodiment, the pixel P may be connected to the A-th scan line (SLa), and the B-th data line (DLb) may be connected to the pixel P.

The gate driver 130 may transmit scan signals SCAN1 through SCANm to scan lines. The gate driver 130 may transmit scan signals SCAN1 through SCANm in synchronization with a vertical synchronization signal (VSYNC).

The source driver 140 may transmit data signals DATA1 through DATAn to data lines in synchronization with scan signals SCAN1 through SCANm. The source driver 140 may transmit data signals DATA1 through DATAn, in response to received image data (e.g., image data ID), to data lines.

Figure 2:
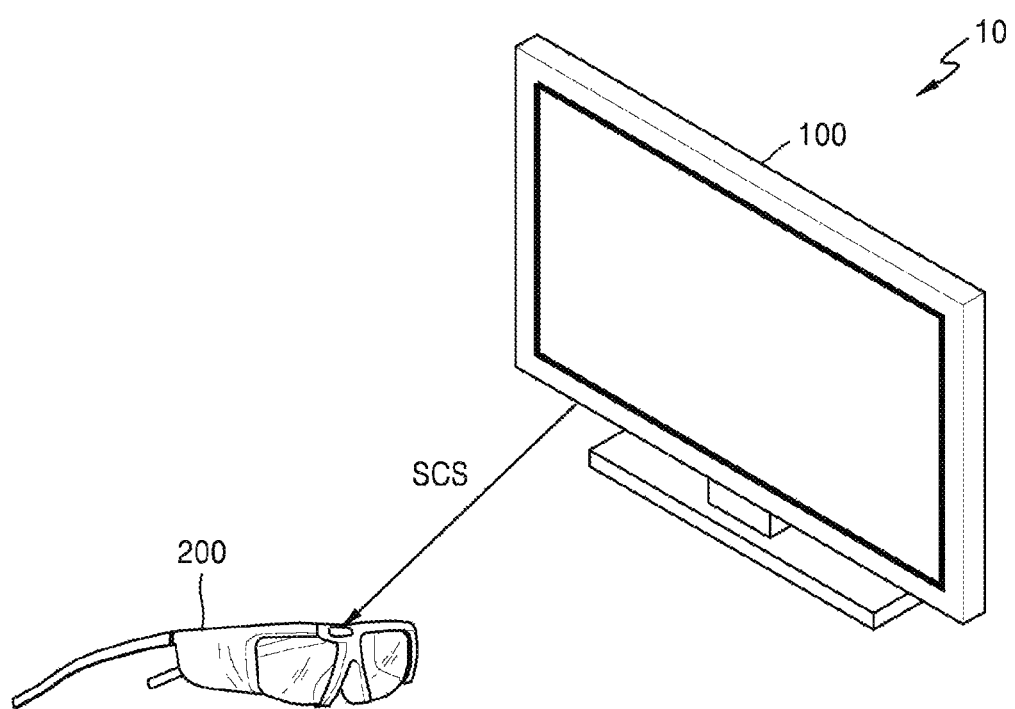
FIG. 2 is a schematic view of a display system according to an exemplary embodiment of the inventive concept.

FIG. 2 is a schematic view of the display system 10 according to an exemplary embodiment of the inventive concept.

Referring to FIG. 2, the display system 10, according to the present embodiment, includes the display apparatus 100 and a pair of shutter glasses 200.

The pair of shutter glasses 200 may synchronize with a changing speed of images displayed on the display apparatus 100, and open and close the shutters for both eyes for some time. For example, when a first image is displayed on the display apparatus 100, the pair of shutter glasses 200 opens the shutters for both eyes to enable a viewer to view the first image. In an embodiment, when a second image is displayed on the display apparatus 100, the pair of shutter glasses 200 closes the shutters for both eyes to stop the viewer from viewing the second image.

In an embodiment, the display apparatus 100 transmits a shutter glasses control signal SCS to the pair of shutter glasses 200. The display apparatus 100 and the pair of shutter glasses 200 may transmit and receive the shutter glasses control signal SCS by various wired or wireless communication between each other. The display apparatus 100 may generate the shutter glasses control signal SCS in synchronization with the image displayed on the display apparatus 100, and transmit the shutter glasses control signal SCS to the pair of shutter glasses 200.

In an embodiment, the pair of shutter glasses 200 includes a shutter for each eye, and a shutter driving unit (e.g., a shutter driving circuit) to control whether to open or close the shutters. The shutter driving unit may send a shutter driving signal to the shutters for both eyes to open or close the shutters according to the shutter glasses control signal SCS received from the display apparatus 100.

In an embodiment, the display system 10, according to the present embodiment, blocks a third or two thirds of an entire image transmitted from the display apparatus 100 through the pair of shutter glasses 200 so that a half or a third of the entire image reaches both eyes of the viewer selectively. Accordingly, flicker may be observed when a driving frequency of the display apparatus 100 is not high enough. To prevent this flicker from being observed, the display apparatus 100 may be driven at a speed higher than a certain level. For example, the pixel P or a backlight of the display apparatus 100 may be driven higher than 120 Hz. In addition, when an embodiment of the present invention is implemented, the pixel P or the backlight of the display apparatus 100 may be driven higher than 180 Hz.

Figure 3:
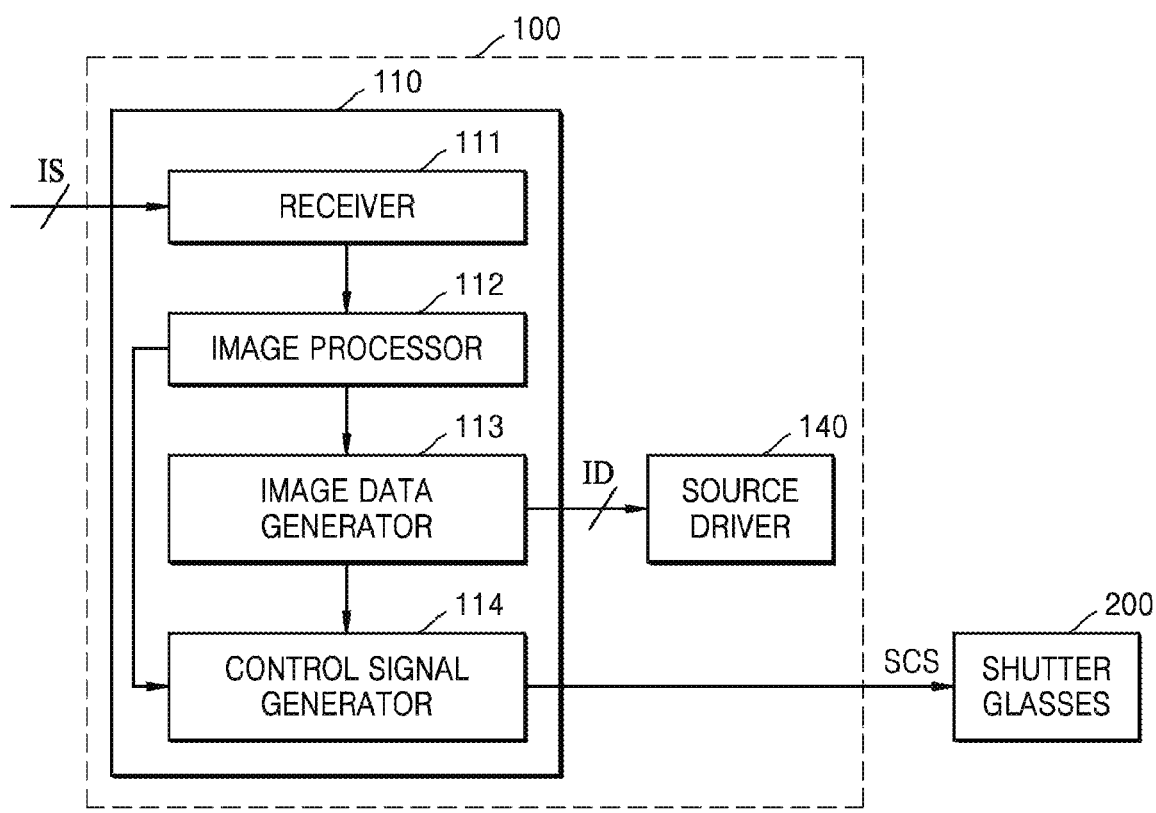
FIG. 3 is a block diagram of a display system according to an exemplary embodiment of the inventive concept.

FIG. 3 is a block diagram of the display system 10 according to an exemplary embodiment of the inventive concept.

Referring to FIG. 3, the control unit 110 of the display apparatus 100 includes a receiver 111, an image processor 112, an image data generator 113, and a control signal generator 114.

The receiver 111 may receive external image content IS. The image content IS may include information to generate an image in a range of visible light perceptible to the human eye through the display apparatus 100. The image content IS may be a digital signal or an analog signal.

The receiver 111 may include a regulator to control a voltage of the image content IS. The receiver 111 may include a noise removing circuit to remove a noise signal in the image content IS. The receiver 111 may include a protection circuit to prevent a signal from emitting in a reverse direction. The receiver 111 may transmit the image content IS to the image processor 112.

The image processor 112 may generate a first image including sequential first frame data and a second image including sequential second frame data. In this embodiment, the first image is an information image corresponding to the image content IS. The first image may be an image in a range of light visible to a viewer of the display apparatus 100. Each of the first frame data may be a datum (for example, a gradation value or a voltage to drive red, green, or blue pixels) to indicate each static image. The first image may be a sequentially arranged image of the static images generated with the first frame data. In an exemplary embodiment, the second image is an image for light therapy. Specific details regarding the second image are explained later with reference to FIG. 4. The image processor 112 may transmit the first and second image signals to the image data generator 113.

Meanwhile, the image processor 112 may determine a luminance of the first image, based on a ratio of a time to display the first image to the total time to display an image on the display 120, and may generate the first frame data by using the ratio. For example, during a half of the total time the image is displayed on the display 120, the first image is displayed but, during the other half, the second image is displayed. In this embodiment, in order to enable the viewer to view the first image of the image content IS with a desired luminance, the image processor 112 may make the luminance of the first image double that of each pixel generated by the image content IS.

Similarly, the image processor 112 may determine the luminance of the first image based on the ratio of opening to closing of the pair of shutter glasses 200 prompted by the shutter glasses control signal SCS, and generate the first frame data by applying the determined luminance. That is, in an embodiment where the first image is displayed just for a half of the total time for viewing the image, a shutter of the pair of shutter glasses 200 will be opened only when the first image is displayed. In this embodiment, in order to enable the viewer to view the first image of the image content IS with the desired luminance, the image processor 112 may make the luminance of the first image double that of each pixel generated by the image content IS.

The image data generator 113 may generate the image data ID which alternately includes the first and second frame data. For example, the image data generator 113 may generate the image data ID by using k-th first frame data which indicates a k-th image frame of the first image. Afterwards, the image data generator 113 may generate the image data ID by using k-th second frame data which indicate a k-th image frame of the second image. The image data generator 113 may generate the image data ID by using (k+1)-th first frame data which indicates a (k+1)-th image frame of the first image. The image data generator 113 may generate the image data ID by using a (k+1)-th second frame data which indicates a (k+1)-th image frame of the second image. This way, the image data generator 113 may generate the image data ID to enable each image frame of the first and second images to be displayed alternately in a sequence.

The control signal generator 114 may generate the shutter glasses control signal SCS. The control signal generator 114 may generate the shutter glasses control signal SCS based on the first and second images generated by the image processor 112. In an embodiment, the image processor 112 determines a resolution of each image and the number of displayed frames per second, when the first and second images are generated. The control signal generator 114 may determine a changing cycle or period of the shutter glasses control signal SCS in synchronization with such resolution or the number of displayed frames per second.

Alternatively, the control signal generator 114 may generate the shutter glasses control signal SCS based on the image data ID generated by the image data generator 113. In an embodiment, the control signal generator 114 generates the shutter glasses control signal SCS image in synchronization with a cycle or period containing the first and second frame data alternately, when the data generator 113 generates the image data ID.

Or, the control signal generator 114 may generate the shutter glasses control signal SCS based on the HSYNC or the VSYNC. In an embodiment, a changing cycle of the image displayed by the display 120 may be identical to the cycle of the HSYNC. Accordingly, the control signal generator 114 may generate the shutter glasses control signal SCS in order to enable the shutter glasses control signal SCS to open or close the shutter at every rising edge or falling edge of the VSYNC. Or, the control signal generator 114 may generate the shutter glasses control signal SCS in order to enable the shutter glasses control signal SCS to open or close the shutter whenever an accumulated number of rising edges or falling edges of the HSYNC becomes identical to the number of pixels in the vertical direction of the display 120.

Through this process, the control signal generator 114 may generate the shutter glasses control signal SCS in order to enable the shutter of the pair of shutter glasses 200 to open when the first image is displayed on the display 120 and the shutter of the pair of shutter glasses 200 to close when the second image is displayed on the display 120. The control signal generator 114 may send the generated shutter glasses control signal SCS to the pair of shutter glasses 200 by wired or wireless communication. For example, the control signal generator 114 may include a transmitter that can be used to wirelessly transmit the generated shutter glasses control signal SCS to a pair of glasses 200.

The receiver 111, the image processor 112, the image data generator 113, and the control signal generator 114 may be each configured on a separate integrated circuit, or may be configured while on an integrated circuit designed to configure other elements of the control unit 110.

A display apparatus 100 according to an exemplary embodiment of the present invention displays a third image, which is an image for a color-weak person, in addition to the first image corresponding to the image content IS and the second image for light therapy. The third image may be generated through the image processor 112. That is, the image processor 112 may generate the third image including sequential third frame data based on the image content IS or the first image.

In this embodiment, the third image is an image for a color-weak person, with at least one of red, green and blue emphasized more than the rest of the colors. Hereinafter, a color-weak person may mean a person who recognizes any color, but is less sensitive to the color, and has a higher color threshold than a color-normal person. A color-weakness may be divided into three types: a red/green deficiency, a blue/yellow deficiency, and a total color-weakness (e.g., completely color blind or monochromacy). The third image, which is an image for a color-blind person, may be an image with appropriate transformation applied to the image content IS or the first image such that the color-weak person may recognize normal colors.

In an embodiment where the first image is Ri, Gi, Bi, and the third image is Ro, Go, Bo, the image processor 112 generates an image for a color-weak person by using the following Math Formula 1.

$$\begin{bmatrix} R_o \\ G_o \\ B_o \end{bmatrix} = \frac{X}{255} \cdot [T] \cdot \begin{bmatrix} R_i \\ G_i \\ B_i \end{bmatrix} \qquad \text{[Math Formula 1]}$$

In this context, X refers to a correction coefficient and T refers to a correction matrix. Ri, Gi, Bi refers to the input the RGB data and Ro, Go, Bo refers to correction RGB data. The correction matrix T may be a coefficient, which is determined depending on the type of color-weak of the person. That is, by contrasting a color which is difficult for color-weak person to recognize and the rest of the colors, it is possible to make the color-weak person recognize the color the way a person who recognizes 3 colors (a normal person) recognizes. The correction matrix T may be a 3×3 matrix, and 9 coefficients of the matrix may be determined through diverse image processing methods. The x/255 may serve the role of diminishing, at a certain rate, the RGB data value of the third image generated by multiplying the correction matrix T and the RGB data of the first image together. In an embodiment, the denominator in the parameter x/255 corresponds to a maximum grayscale value of the image data.

In an embodiment, the image data generator 113 generates image data which includes the first through third frame data sequentially. For example, the image data generator 113 may generate the image data ID by using the k-th first frame data which indicates the k-th image frame of the first image. Afterwards, the image data generator 113 may generate the image data ID by using the k-th second frame data which indicates the k-th image frame of the second image. Afterwards, the image data generator 113 may generate the image data ID by using the k-th third frame data which indicates the k-th image frame of the third image. The image data generator 113 may generate the image data ID by using the (k+1)-th first frame data which indicates the (k+1)-th image frame of the first image. The image data generator 113 may generate the image data ID by using the (k+1)-th second frame data which indicates the (k+1)-th image frame of the second image. The image data generator 113 may generate the image data ID by using the (k+1)-th third frame data which indicates the (k+1)-th image frame of the third image. This way, the image data generator 113 may generate the image data ID to enable each image frame of the first through third images to be displayed alternately in a sequence.

Figure 9:
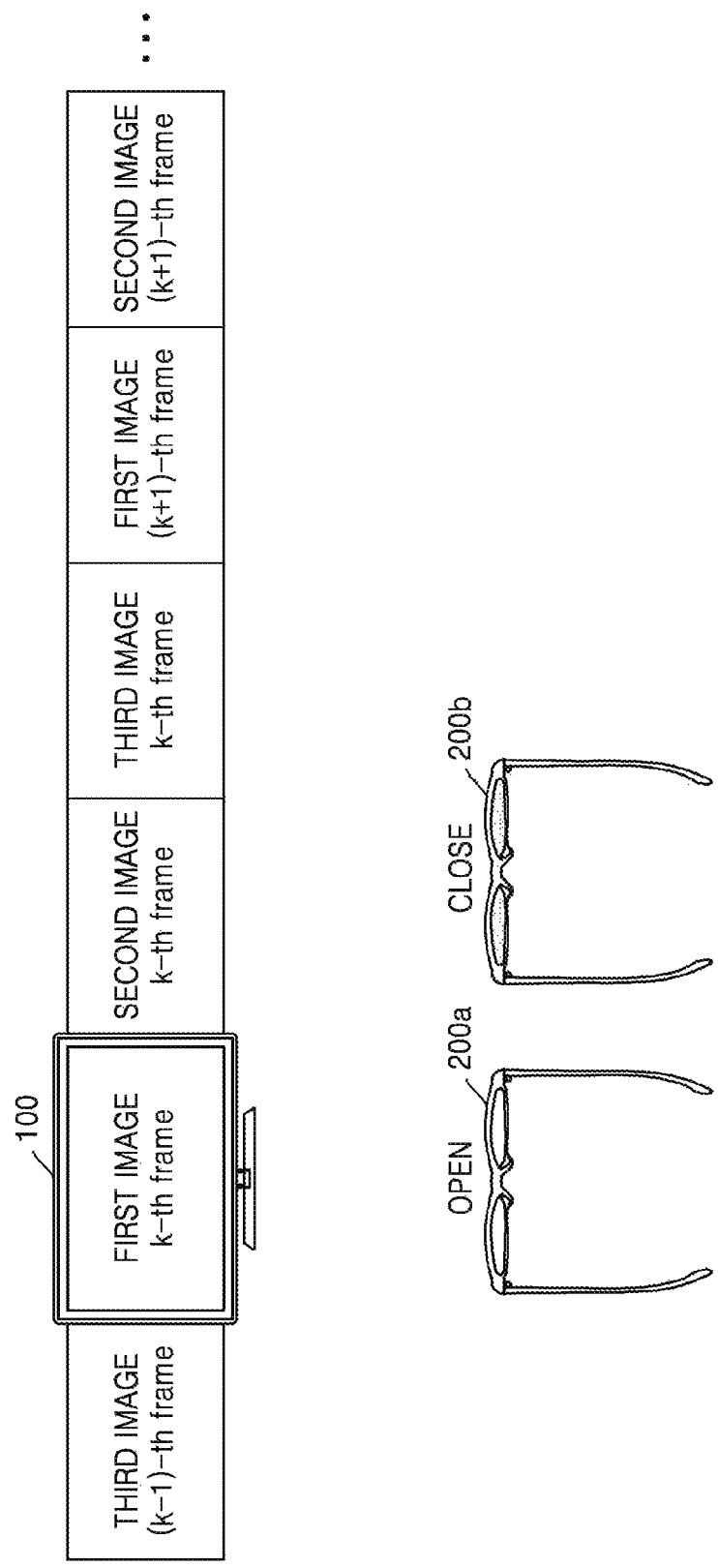

In an embodiment where the display apparatus 100 displays the first image corresponding to the image content IS, the second image, which is an image for light therapy, and the third image, which is an image for a color-weak person, the display system 10 includes the first pair of shutter glasses (200A in FIG. 9) and the second pair of shutter glasses (200B in FIG. 9).

In this embodiment, the control signal generator 114 generates the shutter glasses control signal SCS to control the shutter such that when the first image is displayed on the display 120, the shutter glasses control signal SCS makes the shutters for both eyes of the first pair of shutter glasses 200A open while making the shutters for both eyes of the second pair of shutter glasses 200B closed; when the second image is displayed on the display 120, the shutter glasses control signal SCS makes the shutters for both eyes of the first pair of shutter glasses 200A and the second pair of shutter glasses 200B closed; and when the third image is displayed on the display 120, the shutter glasses control signal SCS makes the shutters for both eyes of the first pair of shutter glasses 200A closed while making the shutters for both eyes of the second pair of shutter glasses 200B open. The control signal generator 114 may send the generated shutter glasses control signal SCS to the pair of shutter glasses 200 by wired or wireless communication.

In an embodiment where the first through third images are displayed on the display apparatus 100 sequentially, a time required to display the first image may be a third of the total time required to display the image on the display 120. In this embodiment, in order to enable the viewer to view the first image through the image content IS with a desired luminance, the image processor 112 makes the luminance of the first image triple that of each pixel generated by the image content IS Likewise, a time required to display the third image may be also a third of the total time required to display the image on the display 120. In this embodiment, in order to enable the color-weak viewer to view the third image through the image content IS with intended luminance, the image processor 112 makes the luminance of the third image triple that of each pixel generated by the image content IS.

Figure 4:
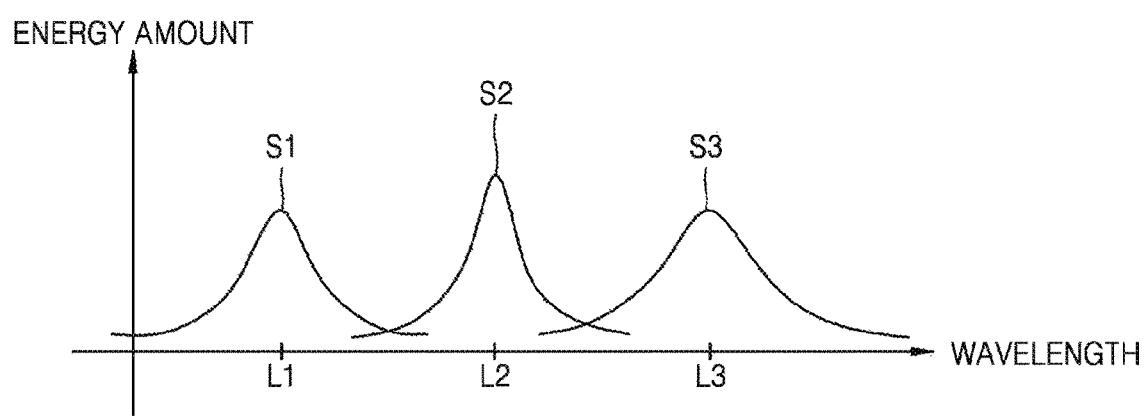
FIG. 4 is a schematic view of an energy amount with respect to a wavelength of light for light therapy, according to an exemplary embodiment of the inventive concept.

FIG. 4 is a schematic view of an energy amount with respect to a wavelength of light for light therapy, according to an exemplary embodiment of the inventive concept.

Referring to FIG. 4, the light for light therapy, according to the present embodiment, includes light represented by a spectrum S1 which outputs a maximum energy amount at a wavelength of L1, light represented by a spectrum S2 which outputs a maximum energy amount at a wavelength of L2, and light represented by a spectrum S3 which outputs a maximum energy amount at a wavelength of L3.

Generally, the display 120 of the display apparatus 100 may emit light in a visible-light range; and when the light is emitted and displayed on the display 120, it is called an image. However, hereinafter, the display 120 may emit light in an infrared range or in an ultraviolet range; and when the light invisible to the human eye is emitted from the display 120, it may also be called an image. For this, pixels P disposed on the display 120 may emit the light in the infrared range or in the ultraviolet range. That is, the pixels P may emit at least a part of infrared light at a wavelength of 700 through 1,000 nanometers and ultraviolet light at a wavelength of 10 through 390 nanometers, in addition to light at a wavelength of 390 through 700 nanometers. In an embodiment where the pixel P is a self-emitting device, the pixel P may include a light-emitting device which may output light having a corresponding wavelength. In an embodiment where the pixel P is not a self-emitting device, the display apparatus 100 includes a light source which outputs light at the same wavelength.

The L1 may be a length in the range of 100-380 nanometers, but is not limited thereto, and may mean a length corresponding to a wavelength of the ultraviolet range. The L2 may be a length in the range of 490-455 nanometers, but is not limited thereto, and may mean a length corresponding to a wavelength of the blue visible light range. The L3 may be a length in the range of 800-1,000 nanometers, but is not limited thereto, and may mean a length corresponding to a wavelength of the infrared range. In FIG. 4, the spectrums S1, S2, and S3 are described as a light-emitting spectrum which emits energy across a certain range of wavelengths, not as a single spectrum which has only a single wavelength. However, the invention is not limited thereto, and spectrums S1, S2, and S3 may be a light-emitting spectrum which is only emitted at a single wavelength.

The second image may be an image which enables light represented by one of the spectrums S1, S2, and S3 to be emitted from the display 120. For example, the second image may be an image which allows light outputting a maximum energy amount at a wavelength of 900 nanometers to be emitted from the display 120. In this case, the second image may be an image which allows light outputting a maximum energy amount in the infrared light range to be emitted from the display 120.

The light which includes at least one of light having the maximum energy amount in the infrared range, light having the maximum energy amount in the ultraviolet range, and light having the maximum energy amount in the blue light range may be the light for performing at least one of the roles of treating cancer, skin disorders, controlling biorhythm, and dealing with depression and skin inflammation. In an exemplary embodiment, the light having the maximum energy amount in the blue light range has a positive effect on skin care.

The image processor 112 may generate the second image which allows the light represented by one of the spectrums S1, S2, and S3 to be emitted by the display 120, depending on a type of the image for light therapy intended to be emitted though the display 120. In this embodiment, the second frame data may be data, each of which represents a static image as with the first frame data, or may be data which includes a control command to output a certain image for light therapy.

Hereinafter, an operation of the display system 10 will be explained by using an exemplary embodiment in which the display system 10 includes the display apparatus 100 and one pair of shutter glasses 200, and the display apparatus 100 displays the first image corresponding to the image content and the second image, which is an image for light therapy.

Figure 5:
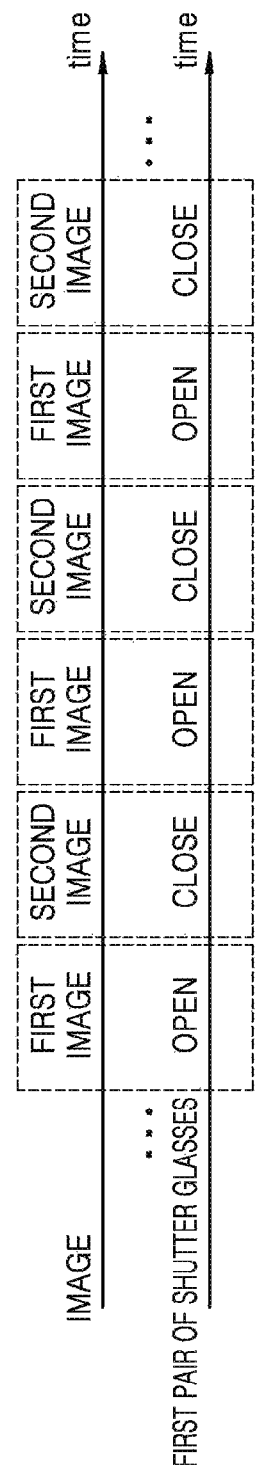
FIGS. 5 through 7 are schematic views of an operation of a display system, according to an exemplary embodiment of the inventive concept.
Figure 6:
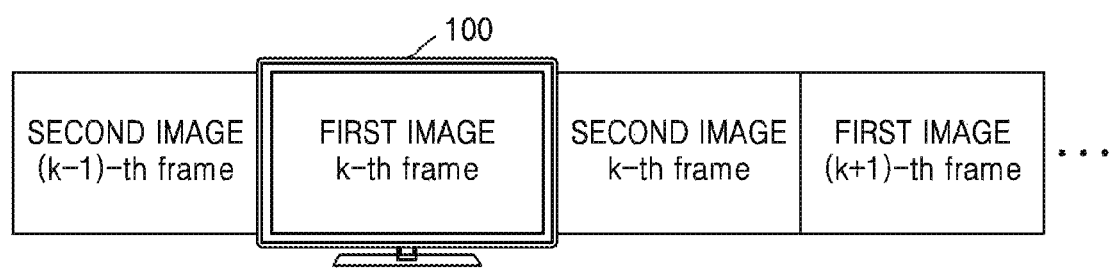
Figure 6:
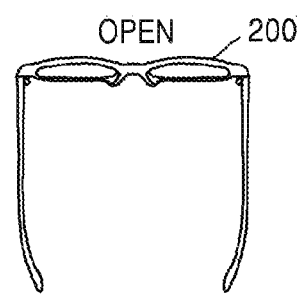
Figure 7:
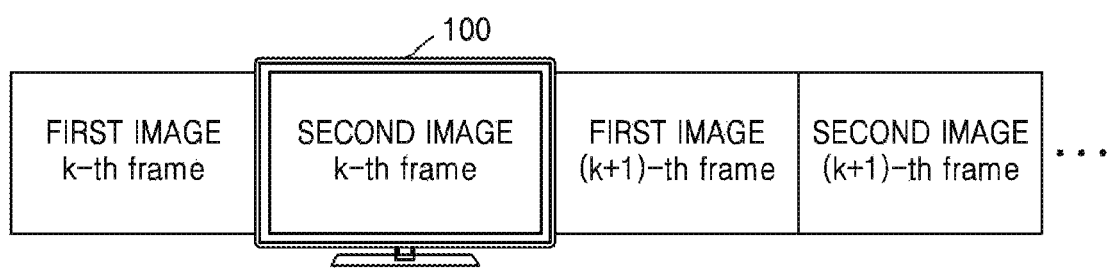
Figure 7:
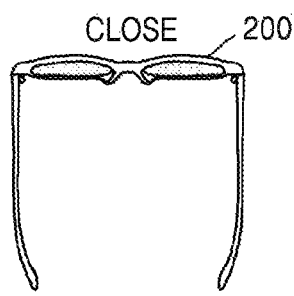

FIGS. 5 through 7 are schematic views of an operation of a display system, according to an exemplary embodiment of the inventive concept.

Referring to FIG. 5, the first image and the second image are displayed alternately on the display 120. In an embodiment, the pair of shutter glasses 200 makes the shutter open when the first image is displayed on the display 120 to enable the viewer to view the first image, while making the shutter closed when the second image is displayed on the display 120 to keep the light emitted by the first image from reaching an eye of the color-weak viewer.

In an embodiment, on the display apparatus 100, a (k−1)-th image frame of the second image, a k-th image frame of the first image, a k-th image frame of the second image, and a (k+1)-th image frame of the first image are displayed sequentially. In this embodiment, as shown in FIG. 6, when the first image is displayed on the display apparatus 100 (for example, when the k-th image frame of the first image is displayed), the shutters for both eyes of the pair of shutter glasses 200 open together. In turn, as shown in FIG. 7, when the second image is displayed on the display apparatus 100 (for example, when the k-th image frame of the second image is displayed), the shutters for both eyes of the pair of shutter glasses 200 are closed together.

Through this process, the display system 10, according to the present embodiment, may enable a viewer who wears the pair of shutter glasses 200 to view the first image without being affected by the second image, which is an image for light therapy of both eyes of the viewer.

Hereinafter, an operation of the display system 10 will be explained by using an exemplary embodiment in which the display system 10 includes the display apparatus 100, the first pair of shutter glasses 200A and the second pair of shutter glasses 200B; and, the display apparatus 100 displays the first image corresponding to the image content IS, the second image, which is an image for light therapy, and the third image, which is an image for a color-weak person.

FIGS. 8 through 11 are schematic views of an operation of a display system, according to another exemplary embodiment of the inventive concept.

Figure 8:
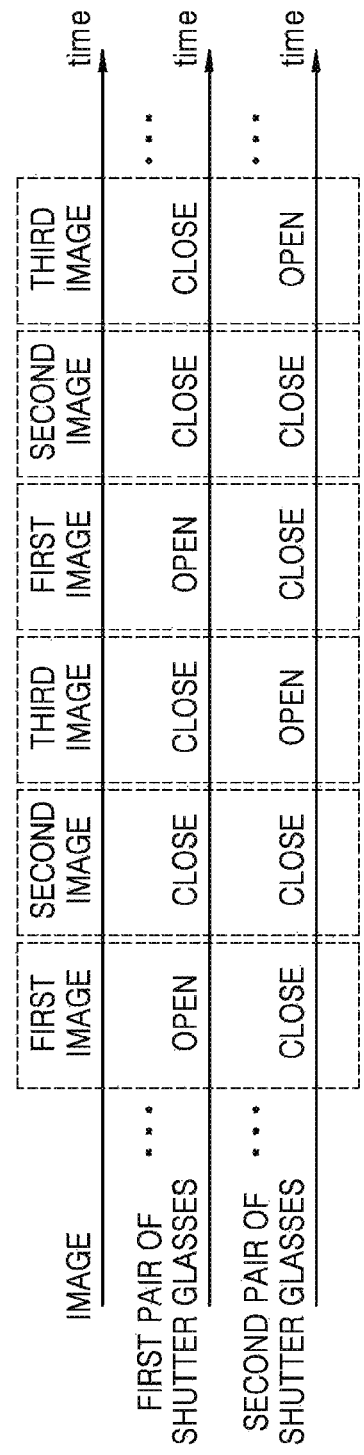
FIGS. 8 through 11 are schematic views of an operation of a display system, according to an exemplary embodiment of the inventive concept.

Referring to FIG. 8, the first through third images are displayed on the display 120 alternately in a sequence. In an embodiment, when the first image is displayed on the display 120, the first pair of shutter glasses 200A makes the shutter open to enable the viewer to view the first image, while making the shutter closed to prevent the light emitted by the second or third image from reaching an eye of the color-weak viewer, when the second or third image is displayed on the display 120. Similarly, when the third image is displayed on the display 120, the second pair of shutter glasses 200B makes the shutter open to enable the viewer to view the third image while making the shutter closed to prevent the light emitted by the first or second image from reaching an eye of the color-weak viewer, when the first or second image is displayed on the display 120.

Figure 10:
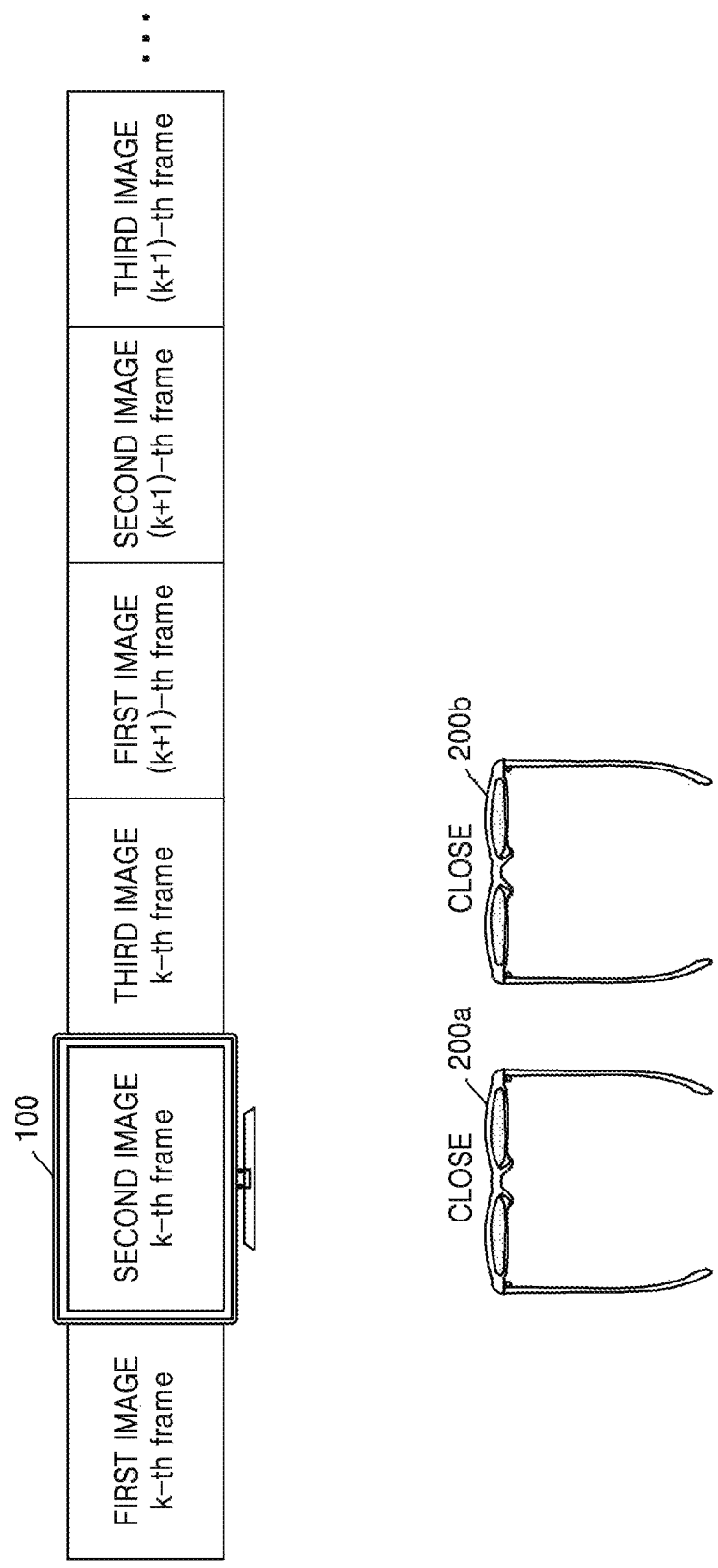
Figure 11:
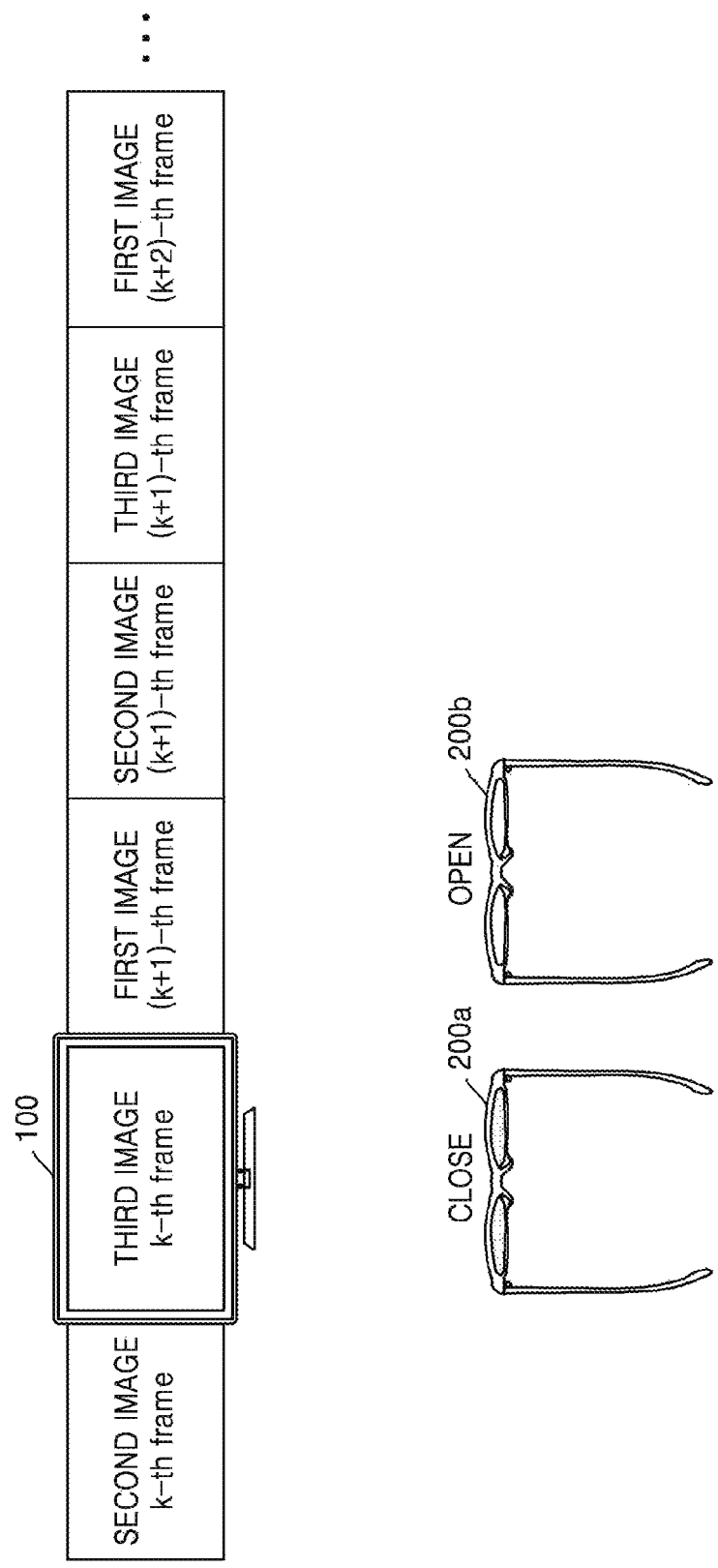

In an embodiment, on the display apparatus 100, a (k−1)-th image frame of the third image, a k-th image frame of the first image, a k-th image frame of the second image, a k-th image frame of the third image and a (k+1)-th image frame of the first image are displayed sequentially. In this embodiment, as shown in FIG. 9, when the first image is displayed on the display apparatus 100 (for example, when the k-th image frame of the first image is displayed), the shutters for both eyes of the first pair of shutter glasses 200A is opened together while the shutters for both eyes of the second pair of shutter glasses 200B is closed together. In turn, as shown in FIG. 10, when the second image is displayed on the display apparatus 100 (for example, when the k-th image frame of the second image is displayed), the shutters for both eyes of the first pair of shutter glasses 200A and the second pair of shutter glasses 200B are closed together. In addition, as shown in FIG. 11, when the third image is displayed on the display apparatus 100 (for example, when the k-th image frame of the third image is displayed), the shutters for both eyes of the first pair of shutter glasses 200A are closed together while the shutters for both eyes of the second pair of shutter glasses 200B are open together.

Through this process, the display system 10, according to the present embodiment, may enable the viewer who wears the first pair of shutter glasses 200A to view the first image corresponding to the image content without being affected by the image for light therapy and the image for a color-weak person. In an embodiment, the display system 10, according to an exemplary embodiment, may enable the viewer who wears the second pair of shutter glasses 200B to view the third image, which is an image for a color-weak person, without being affected by the image for a normal person and the image for light therapy.

In an exemplary embodiment, there are two different shutter glasses control signals, a first shutter glasses control signal that is formatted for the first pair of shutter glasses 200A and a second glasses control signal that is formatted for the second pair of shutter glasses 200B. For example, the first shutter glasses control signal could have a first logic level during an entire first time period at which the first image is displayed, a second logic level during an entire second time period at which the second image is displayed, and the second logic level during an entire third time period at which the third image is displayed, while the second shutter glasses control signal has the second logic level during the first two periods and the first logic level during the third period. For example, the first logic level could be a high level and the second logic level could be a low level. In this embodiment, the two different shutter glasses control signals may additionally include information that is used by the glasses so that they can determine which signal to listen to. For example, the information could indicate that the present signal is to be used with a person with a color weakness or is not to be used with a person with a color weakness. For example, each pair of glasses may include a stored value that indicates whether it is to be used with a person having a color weakness or is not to be used with a person having a color weakness. For example, if the stored value of a pair of glasses indicates it is to be used with a person having a color weakness and it receives a shutter glasses control signal whose information indicates it is not to be used with a person having a color weakness, the glasses can ignore the received shutter glasses control signal. For example, if the stored value of a pair of glasses indicates it is to be used with a person having a color weakness and it receives a shutter glasses control signal whose information indicates it is to be used with a person having a color weakness, the glasses can use the received shutter glasses control signal to control its shutters. In an embodiment, each pair of glasses includes a depressable, slidable, or movable physical button or slider that enables a user to set the value of the corresponding pair to indicate whether it is to be used with a color weak person or is not to be used with a color weak person. For example, the slider could be moved to a first position indicating it is to be used with a person having a color weakness and to a second position indicating it is to be used with person who does not have a color weakness. Thus, the pair of glasses, based on the setting of its slider, can determine which of the shutter glasses control signals to operate on or to ignore.

While one or more exemplary embodiments have been described above with reference to the figures, it will be understood by those of ordinary skill in the art that various changes in form and details may be made therein without departing from the spirit and scope of the inventive concept.

What is claimed is:

1. A display apparatus comprising:
   a display;
   an image processor configured to generate a first image comprising sequential first frame data and a second image comprising sequential second frame data;
   an image data generator configured to generate image data which comprises the first frame data and the second frame data alternately; and
   a control signal generator configured to generate a shutter glasses control signal that opens shutters for both eyes of a first pair of shutter glasses when the first frame data is displayed on the display, and that closes the shutters for both eyes of the first pair of shutter glasses when the second frame data is displayed on the display.

2. The display apparatus of claim 1, further comprising a receiver configured to receive image content, wherein the image processor generates the first image using the image content.

3. The display apparatus of claim 2, wherein the image processor generates a third image comprising sequential third frame data based on the image content, and the third image is an image for a person with a color vision deficiency, with at least one of red, green and blue emphasized more than the rest of the colors.

4. The display apparatus of claim 3, wherein the image data generator generates the image data comprising the first through third frame data sequentially.

5. The display apparatus of claim 4, wherein the control signal generator generates the shutter glasses control signal that opens the shutters for both eyes of the first pair of shutter glasses open and closes the shutters for both eyes of a second pair of shutter glasses, when the first frame data is displayed on the display; that closes the shutters for both eyes of the first pair of shutter glasses and the second pair of shutter glasses, when the second frame data is displayed on the display; and that closes the shutters for both eyes of the first pair of shutter glasses and opens the shutters for both eyes of the second pair of shutter glasses, when the third frame data is displayed on the display.

6. The display apparatus of claim 2, wherein the image processor determines a luminance of the first image, based on a ratio of a time to display the first frame data to the total time to display an image on the display.

7. The display apparatus of claim 2, wherein the image processor determines a luminance of the first image based on a ratio of opening to closing of the shutters of the first pair of shutter glasses driven by the shutter glasses control signal.

8. The display apparatus of claim 1, wherein the second image is an image for light therapy that enables at least one of light having a maximum energy amount in an infrared range, light having a maximum energy amount in an ultraviolet range, and light having a maximum energy amount in a blue light range to be emitted by the display.

9. The display apparatus of claim 1, wherein the second image is a light therapy image to be emitted by the display for performing at least one of treating a skin disorder, controlling biorhythm, treating depression, treating a skin inflammation, and treating cancer.

10. A display system comprising:
the display apparatus of claim 1; and
the first pair of shutter glasses that opens or closes the shutters for both eyes simultaneously by receiving the shutter glasses control signal.

11. A display system comprising:
the display apparatus of claim 5;
the first pair of shutter glasses that opens or closes its shutters simultaneously by receiving the shutter glasses control signal; and
the second pair of shutter glasses that opens or closes its shutters simultaneously by receiving the shutter glasses control signal.

12. A display apparatus comprising:
a display configured to display a first image, a second image, and a third image alternately; and
a control signal generator configured to generate a shutter glasses control signal that opens first shutters for both eyes of a first pair of shutter glasses and closes second shutters for both eyes of a second pair of shutter glasses when the first image is displayed on the display, that closes the first and second shutters when the second image is displayed on the display, and that closes the first shutters and opens the second shutters when the third image is displayed.

13. The display apparatus of claim 12, wherein the first image comprises red, green, and blue color data, the second image is a light therapy image, and the third image is converted from the first image and emphasizes one of the red, green and blue color data more than the rest of the color data.

14. The display apparatus of claim 13, wherein the light therapy image causes the display to emit light in one of an infrared, an ultraviolet, or a blue light range.

15. The display apparatus of claim 13, wherein the display includes self-emissive pixels.

16. The display apparatus of claim 13, wherein the light therapy image causes the display to emit light in one of a first range of 100 to 380 nanometers, a second range of 454 to 490 nanometers and a third range of 800 to 1000 nanometers.

17. A display apparatus comprising:
a display configured to display a first image and a second image alternately; and
a control signal generator configured to generate a shutter glasses control signal that opens shutters for both eyes of a first pair of shutter glasses when the first image is displayed on the display, and that closes the shutters for both eyes of the first pair of shutter glasses when the second image is displayed on the display.

18. The display apparatus of claim 17, further comprising:
a receiver configured to receive image content; and an image processor configured to generate the first image using the image content; and
wherein the second image is an image for light therapy that enables at least one of light having a maximum energy amount in an infrared range, light having a maximum energy amount in an ultraviolet range, and light having a maximum energy amount in a blue light range to be emitted by the display.

19. The display apparatus of claim 18, wherein the image processor generates a third image based on the image content; the third image is an image for person with a color vision deficiency, with at least one of red, green and blue emphasized more than the rest of the colors; and the display displays the first through third images alternately.

20. The display apparatus of claim 19, wherein the control signal generator generates the shutter glasses control signal that opens the shutters for both eyes of the first pair of shutter glasses open and closes the shutters for both eyes of a second pair of shutter glasses, when the first image is displayed on the display; that doses the shutters for both eyes of the first pair of shutter glasses and the second pair of shutter glasses, when the second image is displayed on the display; and that doses the shutters for both eyes of the first pair of shutter glasses and opens shutters for both eyes of the second pair of shutter glasses open, when the third image is displayed on the display.

* * * * *